United States Patent [19]

Reed

[11] Patent Number: 5,146,024
[45] Date of Patent: Sep. 8, 1992

[54] HYDROALKYLATION OF AROMATIC HYDROCARBONS

[75] Inventor: Larry E. Reed, Bartlesville, Okla.

[73] Assignee: Phillips Petroleum Company, Bartlesville, Okla.

[21] Appl. No.: 703,071

[22] Filed: May 20, 1991

[51] Int. Cl.$^5$ ............................................. C07C 2/66
[52] U.S. Cl. .................................... 585/270; 585/268; 585/269; 585/446
[58] Field of Search ...................... 585/270, 268, 269

[56] References Cited

U.S. PATENT DOCUMENTS 3,412,165  11/1968  Slaugh et al. ...................... 585/270
3,760,017  9/1973  Arkell et al. ........................ 585/270
3,760,019  9/1973  Crome, Jr. et al. ................. 585/270
4,094,918  6/1978  Murtha et al. .................. 260/668 R

*Primary Examiner*—Asok Pal
*Attorney, Agent, or Firm*—K. K. Brandes

[57] ABSTRACT

A process for converting aromatic hydrocarbons (in particular benzene) to cycloalkyl-substituted aromatic hydrocarbons (in particular cyclohexylbenzene) in the presence of free hydrogen and a palladium-promoted zeolite catalyst is carried out in the presence of carbon monoxide as process modifier (so as to enhance the selectivity to the cycloalkyl-substituted aromatic hydrocarbon).

11 Claims, No Drawings

HYDROALKYLATION OF AROMATIC HYDROCARBONS

BACKGROUND OF THE INVENTION

This invention relates to an improved process for hydroalkylating aromatic hydrocarbons, in particular the conversion of benzene and free hydrogen to cyclohexylbenzene, in the presence of a noble metal-promoted zeolite catalyst.

The hydroalkylation of aromatic hydrocarbons in the presence of catalysts which comprise a nickel- and rare earth-treated zeolite and palladium as promoter is known and has been described in U.S. Pat. Nos. 4,094,918 and 4,177,165. The present invention is an improved hydroalkylation process which produces the desired cycloalkylated aromatic hydrocarbons at a higher selectivety than the prior art process.

SUMMARY OF THE INVENTION

It is an object of this invention to enhance the selectivity of the catalytic conversion of aromatic hydrocarbons (such as benzene) and hydrogen to cycloalkyl-substituted aromatic hydrocarbons (such as cyclohexylbenzene) by employing a modifying agent.

In accordance with this invention, in a process of at least partially converting at least one aromatic hydrocarbon containing 6-9 carbon atoms per molecule and free hydrogen to at least one monocycloalkyl-substituted aromatic hydrocarbon in the presence of a catalyst comprising (a) at least one Group VIII metal promoter selected from the group consisting of platinum metal and compounds of platinum and (b) an acidic, nickel- and rare earth-treated crystalline zeolite as support, the improvement comprises the presence of carbon monoxide at a molar ratio of carbon monoxide to free hydrogen not to exceed about 0.5:1 (i.e., at a ratio of about 0.5:1 or less).

DETAILED DESCRIPTION OF THE INVENTION

The catalyst composition employed in the process of the instant invention can be briefly described as a crystalline zeolite which has been cation-exchanged with rare earth, nickel and ammonium compounds, followed by a calcination step and an impregnation step with rhodium or palladium compounds or mixtures thereof. Although not absolutely necessary, it is preferred that the above catalyst be treated with hydrogen prior to the introduction of the aromatic hydrocarbon feed into the hydroalkylation process zone.

The support material for the catalyst composition employed in the instant invention is a crystalline zeolite which has been treated under cation exchange conditions with a mixture of rare earth compound(s), nickel compound(s) and ammonium compound(s) such that the cation metal content of the zeolite is partially exchanged. Generally the cationic material in the zeolite is an alkali metal which is sufficiently removed by cation-exchange such that the remaining alkali metal content after the cation-exchange step ranges from about 0.01 to about 2 percent by weight, preferably about 0.02-1 percent by weight. Any suitable crystalline zeolite can be used in accordance with the present invention. Presently preferred are the Type X or Type Y crystalline zeolites, which are sometimes called molecular sieves because of their essentially uniform pore diameters. Some suitable Type Y synthetic crystalline zeolites are described for example in U.S. Pat. No. 3,130,007, some suitable Type X zeolites are described in U.S. Pat. No. 2,882,244, and some Type L zeolites are described in U.S. Pat. No. 3,216,789. Such materials are presently commercially available, as for example zeolite SK-40 (Type Y) and zeolite 13 X (Type X) from Union Carbide Corporation, Danbury, CT. Presently more preferred are Type X zeolites.

The alkali metal form of the crystalline zeolites usually comprises sodium or potassium as the alkali metal (preferably sodium), and said zeolites are treated under cation exchange conditions with a mixture of rare earth, nickel and ammonium compounds in accordance with the present invention in order to provide a suitable support material for the preparation of the catalyst compositions used in the process of the invention.

It is contemplated that any of the readily available rare earth metal compounds (also referred to as Lanthanide metal compounds) can be employed in the cation exchange solution. Generally, the compounds used are those in which the rare earth metal-containing ion is present in the cationic state. Representative rare earth metal compounds include nitrates, bromides, acetates, chlorides, iodides, sulfates and mixtures thereof of one or more of the rare earth metals including cerium, lanthanum, praseodymium, neodymium, samarium, europium, gadolinium, terbium, dysprosium, holmium, erbium, thulium, ytterbium, and lutetium. Compounds of the rare earth metals named above may be employed singly; however, it is often convenient to employ mixtures of two or more than two rare earth metal compounds. For example, mixtures of rare earth metal compounds such as the chlorides or nitrates of lanthanum, cerium, praseodymium, neodymium, samarium and gadolinium are available commercially at a relatively low cost and may be effectively employed.

Any convenient ammonium compound can be employed in the zeolite treatment step, although the chloride is preferred because it is inexpensive and readily available. The ion-exchange with the ammonium compound can be carried out before or concurrently with the ion-exchange with the rare earth metal and nickel compounds. The weight ratio of ammonium compound to nickel and rare earth compounds in the aqueous exchange solution(s) can be selected over a broad range. Generally the weight ratio of ammonium compound to nickel and rare earth compounds combined is within the range of from about 0.05:1 to about 20:1, preferably from about 0.2:1 to about 5:1. The concentration of rare earth compounds in the aqueous exchange solution can be varied over a wide range and exchange conditions can be adjusted accordingly such that the rare earth content of the ion exchanged crystalline zeolite can be selected over a broad range. Generally, the content of the final catalyst composite in terms of the rare earth elements is about 2 to about 25 weight percent, preferably about 5 to 20 weight percent. The alkali metal content, for example sodium, of the exchanged catalyst support is partially removed by the ion exchange step and the alkali metal is generally in the range of from about 0.01 to about 2 percent by weight, preferably from about 0.02 to about 1 percent by weight.

The nickel compounds which will be employed in admixture with the above-named rare earth metal compounds are those wherein the nickel ion is present in the cationic state. Some suitable compounds representative of the nickel compounds which can be used in the invention include the nitrates, bromides, acetates, chlorides, iodides, sulfates and mixtures thereof. The nickel content in the final composition can also be selected over a broad range. Generally the composition will comprise about 0.01 to about 12 weight percent nickel, preferably about 2 to about 7 percent by weight Ni.

A zeolite, preferably a Type X or a Type Y zeolite, is treated with aqueous solutions of ammonium, rare earth metal and nickel compounds, either sequentially or concurrently, so as to replace a portion of the alkali metal content of the zeolite. This cation-exchange process can be carried out in a batch or continuous fashion, generally at a temperature of 80° to 100° C., under conditions such that from about 0.1 to about 0.5 of the volume of aqueous salts solution per volume of zeolite is in contact with said zeolite per hour. Under these conditions, the exchange process can be completed in about 1–50 hours to achieve the desired levels of rare earth, nickel and ammonium ions in the zeolite. The exchanged zeolite is then washed free of excess ions from the exchange step with water. The excess wash water is removed by drying the zeolite, generally at a temperature ranging from about 100° to about 200° C., just prior to calcination. The dried material can be calcined before or after the impregnation with the rhodium or palladium compound (to be described below), e.g., at a temperature of about 200° to about 550° C. (preferably about 300°–400° C., in order to calcine the zeolite and convert the ammonium cations to the hydrogen form. Usually, the calcination is conducted until a constant weight of the zeolitic material is attained, generally for a time period of about 2 to about 10 hours. The calcined zeolite is then cooled in ambient air, i.e., under conditions of normal humidity.

The above-described support is impregnated with a solution of at least one palladium compound, followed by evaporation of the solvent used in the impregnation step. Evaporation of the solvent can be conducted under vacuum if desired. Suitable solvents include water, alcohols, such as ethanol, ketones, such as acetone, and the like. Some of the various palladium compounds suitable for use in the impregnation step include palladium(II) acetylacetonate, palladium(II) chloride, palladium(II) iodide and palladium(II) nitrate. The palladium content in the dried catalyst composition can be selected over a broad range. Generally the palladium content ranges from 0.01 to about 1.5 percent by weight, preferably from about 0.3 to 0.8 percent by weight Pd.

The hydroalkylation of aromatic hydrocarbon of this invention produces cycloalkyl-substituted aromatic hydrocarbons. Some of the feedstocks which are suitable for use in the present invention are aromatic compounds, i.e., monocyclic aromatic hydrocarbons and alkyl-substituted monocyclic aromatic hydrocarbons. Some specific examples of these are benzene, toluene, xylenes, and the like, and mixtures thereof. The aromatic hydrocarbon feedstocks should be essentially free of sulfur-containing compounds and other known poisons for hydrogenation catalysts. However, small amounts of water, e.g., 20–50 ppm, in the feedstock are not considered detrimental.

The invention is particularly valuable for the conversion of benzene to cyclohexylbenzene. Cyclohexylbenzene is known as a valuable solvent and chemical intermediate. It can be converted in high yield to phenol and cyclohexanone by autooxidation with subsequent acid treatment. It is also useful as an intermediate in the production of adipic acid and caprolactam.

The aromatic hydrocarbon feedstock, hydrogen gas and carbon monoxide (the latter being used as a process modifier) are fed to the catalyst-containing reaction zone operated under a wide range of conditions. The liquid hourly space velocity of the aromatic hydrocarbon feed (LHSV; expressed in volume feed per volume catalyst per hour) generally ranges from about 1 to about 100, the total reaction pressure generally ranges from about 345 to about 10,350 kPa (about 50 to about 1500 psig), the hydrogen feed rate generally is such as to provide a molar ratio of $H_2$ to aromatic feed hydrocarbon (preferably benzene) of about 0.1:1 to about 10:1, the carbon monoxide feed rate generally is such as to provide a molar ratio of carbon monoxide to free hydrogen of about 0.01:1 to about 0.3:1, and the reaction temperature generally ranges from about 100° to about 250° C. Preferred operating conditions include a liquid hourly space velocity (LHSV) of the aromatic hydrocarbon feed in the range of about 5 to about 30, a total reaction pressure in the range of about 1,380 to about 4,830 kPa (about 200 to about 700 psig), a molar ratio of $H_2$ to aromatic feed hydrocarbon (preferably benzene) in the range of about 0.2:1 to about 1:1, a molar ratio of CO to $H_2$ in the range of about 0.02:1 to about 0.1:1, and a reaction temperature in the range of about 140° to about 200° C.

The hydroalkylation reaction is conveniently carried out by having the above-described catalyst in a fixed bed reactor and then contacting said catalyst with the aromatic hydrocarbon feed, free hydrogen and carbon monoxide in an upflow or downflow arrangement. It is also possible to operate at a countercurrent flow of the $H_2$/CO gases and the aromatic hydrocarbon feed over the catalyst in the reaction zone, or to carry out the hydroalkylation reaction under batch conditions (e.g., in an autoclave). Hydrogen gas and carbon monoxide gas can be introduced into the reaction zone separately or as a gas mixture.

The reaction mixture from the reaction zone can usually be conveniently separated into the desired components by simple fractional distillation, and recycle of the unreacted feedstock and unreacted hydrogen can be accomplished as desired. The hydroalkylation products can be further purified as desired after separation from unreacted feedstock.

It is generally desirable to pretreat the catalyst with hydrogen gas prior to contacting the catalyst with the aromatic hydrocarbon. The hydrogen pressure and feed rate for the pretreating (reducing) step generally is the same as that to be employed when contacting the aromatic hydrocarbon with the catalyst. This pretreating step generally requires a temperature of about 200°–350° C. and a time period of about 10 minutes to about 1 hour.

The following examples are provided to further illustrate this invention and are not to be considered as unduly limiting the scope of this invention.

EXAMPLE

The catalyst which was utilized in the hydroalkylation tests described below was prepared as follows. 200 g of a Type X crystalline zeolite (1/16" 13 X molecular sieve extrudate, provided by the Davison Chemical Division of W. R. Grace and Company, Baltimore, MD) was mixed with a first ion-exchange solution containing 250 g $NH_4Cl$ in 1 liter of water. The mixture was stirred for 2 hours at a temperature of 85°–90° C. The used NH₄Cl solution was discarded and the ion-exchange procedure was repeated twice with a fresh NH₄Cl solution. The NH₄-exchanged zeolite was washed three times with water at a temperature of 85°–90° C. The washed NH₄-exchanged zeolite was then treated with a second ion-exchange solution containing 100 g Ni(NO₃)₂.6H₂O, 100 g La(NO₃)₃.6H₂O and 100 g Ce(NO₃)₃.6H₂O in 1 liter of water. The ion-exchange procedure with this second ion-exchange solution was substantially the same as the above-described first ion-exchange step. The thus-twice ion-exchanged catalyst was washed three times with water at a temperature of 85°–90° C. and dried overnight at 110° C.

50 g of the dry, twice ion-exchanged zeolite was impregnated with a solution of 0.705 g Pd(NH₃)₄(NO₃)₂ in 10.8 g H₂O. The Pd-impregnated zeolite was dried under a heat lamp for 1 hour, heated in air for 3 hours at 150° C., calcined in air for 3 hours at 400° C., and finally reduced in hydrogen gas for 2 hours at 300° C. The thus-prepared catalyst contained about 0.5 weight-% Pd.

The above-described catalyst was utilized in the hydroalkylation of benzene. In a typical hydroalkylation run, a 300 cc stainless steel autoclave reactor was filled with 7.5 grams of the catalyst described above and 200 grams of benzene. Thereafter, the content of the autoclave was stirred and heated to about 325° F. and pressured with about 350 psig H₂. The CO pressure was either 0 psig (in control runs) or 15 psig CO (in invention runs). At various time intervals (usually about every half hour), a small sample of the reaction mixture was withdrawn (by opening a valve located at the head of the autoclave) and analyzed by means of a gas chromatograph. Test results are summarized below.

TABLE

| CO Present | % Benzene Conversion | Selectivity (%) To | | |
|---|---|---|---|---|
| | | Cyclohexyl-benzene | Cyclo-hexane | Dicyclohexyl-benzene |
| NO (Control) | 6.9 | 65.51 | 30.86 | 2.87 |
| | 10.3 | 65.29 | 31.41 | 2.37 |
| | 19.8 | 61.73 | 34.27 | 3.37 |
| | 27.2 | 60.51 | 33.97 | 4.30 |
| | 46.9 | 53.59 | 37.38 | 7.53 |
| YES (Invention) | 6.3 | 86.55 | 9.02 | 2.53 |
| | 10.9 | 84.88 | 9.12 | 4.06 |
| | 19.2 | 81.69 | 9.81 | 6.16 |
| | 27.4 | 78.36 | 11.07 | 7.89 |
| | 47.2 | 71.14 | 10.69 | 15.59 |

Test data in the above table clearly show that the presence of CO as a modifier during the hydroalkylation of benzene significantly enhanced the selectivity to the desired product, cyclohexylbenzene.

Reasonable variations and modifications are possible within the scope of the disclosure of the invention and the appended claims.

That which is claimed is:

1. In a process of at least partially converting at least one aromatic hydrocarbon-containing 6–9 carbon atoms per molecule and free hydrogen to at least one monocycloalkyl-substituted aromatic hydrocarbon in the presence of a catalyst comprising (a) at least one Group VIII metal promoter selected from the group consisting of palladium metal and palladium compounds and (b) an acidic, nickel- and rare earth-exchanged crystalline zeolite as support,
   the improvement which comprises the presence of carbon monoxide at a molar ratio of carbon monoxide to free hydrogen which does not exceed about 0.5:1.

2. A process in accordance with claim 1, wherein the molar ratio of free hydrogen to said at least one aromatic hydrocarbon containing 6–9 carbon atoms per molecule is in the range of about 0.1:1 to about 10:1, and the molar ratio of carbon monoxide to free hydrogen in the range of about 0.01:1 to about 0.3:1.

3. A process in accordance with claim 1, wherein said at least one aromatic hydrocarbon is benzene and said at least one monocycloalkyl-substituted hydrocarbon is cyclohexylbenzene.

4. A process in accordance with claim 3, wherein the molar ratio of free hydrogen to benzene is in the range of about 0.1:1 to about 10:1 and the molar ratio of carbon monoxide to free hydrogen is in the range of about 0.01:1 to about 0.3:1.

5. A process in accordance with claim 3, wherein said process is carried out at a reaction temperature of about 100° C. to about 250° C., a total reaction pressure of about 50 psig to about 1500 psig, a molar ratio of free hydrogen to benzene in the range of about 0.1:1 to about 10:1, and a molar ratio of carbon monoxide to free hydrogen in the range of about 0.01:1 to about 0.3:1.

6. A process in accordance with claim 5, wherein said process is carried out at a reaction temperature of about 140° C. to about 200° C., a total reaction pressure of about 200 to about 700 psig, a molar ratio of free hydrogen to benzene is in the range of about 0.2:1 to about 1:1, and a molar ratio of carbon monoxide to free hydrogen is in the range of about 0.02:1 to about 0.1:1.

7. A process in accordance with claim 5, wherein the liquid hourly space velocity of benzene is in the range of about 1 to about 100 volume benzene per volume catalyst per hour.

8. A process in accordance with claim 1, wherein said crystalline zeolite is selected from the group consisting of Type X and Type Y zeolites, and the palladium content in said catalyst is about 0.01 to about 1.5 percent by weight of Pd.

9. A process in accordance with claim 1, wherein said crystalline zeolite is selected from the group consisting of Type X and Type Y zeolites, the palladium content in said catalyst is about 0.01 to about 1.5 percent by weight of Pd, said at least one aromatic hydrocarbon is benzene, and said at least one monoalkyl-substituted aromatic hydrocarbon is cyclohexylbenzene.

10. A process in accordance with claim 9, wherein said crystalline zeolite is a Type X zeolite and the palladium content in said catalyst is about 0.3 to about 0.7 percent by weight of Pd.

11. A process in accordance with claim 9, wherein said catalyst contains about 2 to about 25 percent by weight of rare earth element, about 0.01 to about 2 weight percent by weight of alkali metal, and about 0.01 to about 12 percent by weight of nickel.

* * * * *